United States Patent [19]

Limbach et al.

[11] Patent Number: 4,629,697
[45] Date of Patent: Dec. 16, 1986

[54] TEST SYSTEM AND PROCEDURE FOR THE DETERMINATION OF NAD (P) H

[75] Inventors: Berthold Limbach, Seeheim; Roland Helger, Darmstadt, both of Fed. Rep. of Germany

[73] Assignee: Merck Patent Gesellschaft mit beschränkter Haftung, Darmstadt, Fed. Rep. of Germany

[21] Appl. No.: 564,866

[22] Filed: Dec. 23, 1983

[30] Foreign Application Priority Data

Dec. 24, 1982 [DE] Fed. Rep. of Germany ....... 3247894

[51] Int. Cl.$^4$ .......................... C12Q 1/32; C12Q 1/62
[52] U.S. Cl. ......................................... 435/26; 422/56; 435/10; 435/805; 435/810; 436/904
[58] Field of Search .................. 435/10, 12, 25, 26, 435/805, 810; 422/56; 436/904

[56] References Cited

U.S. PATENT DOCUMENTS

| | | | |
|---|---|---|---|
| 3,732,147 | 5/1973 | Fosker et al. | 435/26 |
| 3,929,580 | 12/1975 | Forgione et al. | 435/26 |
| 4,056,485 | 11/1977 | Adolf et al. | 435/26 |
| 4,141,688 | 2/1979 | Morris et al. | 544/102 X |
| 4,271,265 | 6/1981 | Deneke et al. | 435/16 |
| 4,394,444 | 7/1983 | Cameron et al. | 435/11 |
| 4,427,771 | 1/1984 | Misaki et al. | 435/22 |
| 4,490,465 | 12/1984 | Limbach et al. | 435/14 |

FOREIGN PATENT DOCUMENTS

| | | | |
|---|---|---|---|
| 52-022993 | 2/1977 | Japan | 435/26 |
| 54-037798 | 3/1979 | Japan | 435/26 |

*Primary Examiner*—Sidney Marantz
*Assistant Examiner*—Cynthia Lee Foulke
*Attorney, Agent, or Firm*—Millen & White

[57] ABSTRACT

A test system having an extended range of measurement and an appropriate procedure for the determination of NAD(P)H or of substrates or enzymes which react to form or consume NAD(P)H in fluids is provided. The test system contains, at one and the same time, several substances acting independently of one another as electron acceptors with respect to NAD(P)H and having different electrochemical potentials. Addition of the test system to the sample solution gives rise to different end products which can be analytically differentiated and which are evaluated visually or by other techniques of measurement.

20 Claims, 2 Drawing Figures

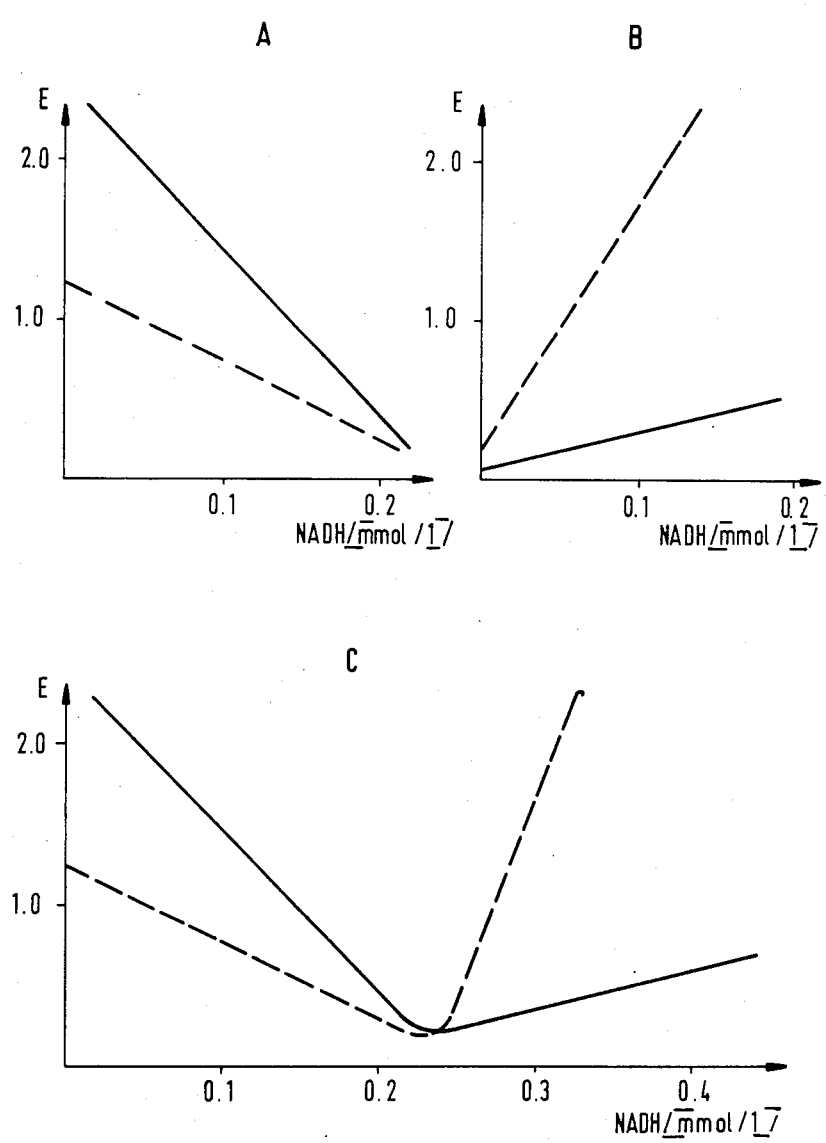

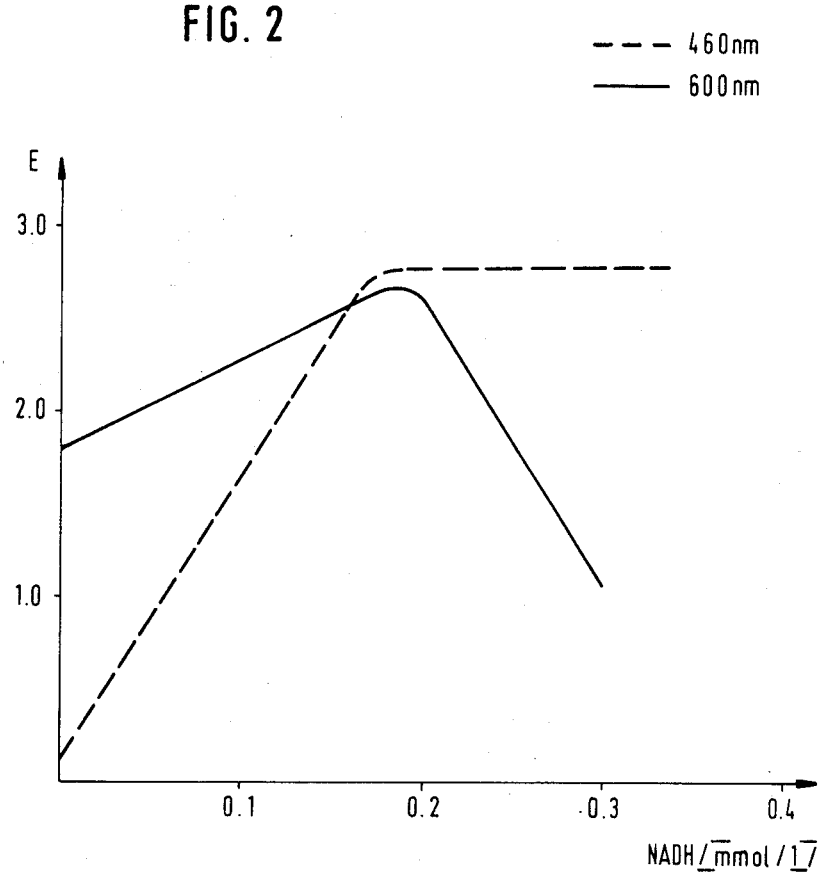

TEST SYSTEM AND PROCEDURE FOR THE DETERMINATION OF NAD (P) H

BACKGROUND OF THE INVENTION

This invention relates to a test system and a procedure having an extended range of measurement for the determination of NAD(P)H or of substrates or enzymes which react with the formation or consumption of NAD(P)H.

In the majority of cases, the determination of clinical parameters is carried out using highly specific dehydrogenase reactions during the course of which NAD(P)H is indirectly or directly formed or consumed. The amount, absolute or per unit of time, of NAD(P)H reacted thereby is a measure of the concentration in a fluid of the substance to be investigated.

The dehydrogenase reaction has proved to be especially advantageous in respect of both stoichiometry and a low susceptibility to interference. On the other hand, it is a disadvantage that, due to the absorption properties of the coenzyme molecule, evaluation of the reaction for measurement is only possible using photometers with a UV measurement range; purely visual evaluations cannot be carried out. The latter are only made possible by coupling the actual reaction which forms NAD(P)H to a color reaction. A large number of procedures achieve this by direct transfer, or transfer using electron transfer agents, such as phenazine methosulphate or diaphorase, of the redox equivalents to a variety of redox indicators. The latter substances include, for example, cytochromes, complexed or chelated iron ions, dichlorophenol-indophenol, tetrazolium salts and the like. Coupling the reaction for measurement to a reaction sequence is also known (See, e.g., German Auslegeschrift No. 1,598,263, or European Patent Specification No. 54,146). The formation of a dyestuff takes place via a substance formed as an intermediate. A sequential course of reactions, in which each product from the first part reaction is the starting substance for the second and so on, is common to all these systems.

A procedure is described in German Patent Application No. P 32 11 167 in which a substance to be determined is reacted to give a variety of products which can be differentiated. Compared with the conventional tests, a wider range of measurement with the same accuracy of measurement is obtained. This is achieved by using several enzyme systems which, independently of one another, react with the same substance to be determined, one system being a NAD-dependent dehydrogenase and another being a NAD-independent dehydrogenase. A disadvantage of this procedure is that the NAD-independent enzymes necessary for a major proportion of the substances to be investigated in clinical diagnostics are not commercially available, in contrast to the corresponding NAD-dependent enzymes.

SUMMARY OF THE INVENTION

It is an object of this invention to provide a test system for the determination of NAD(P)H, which has a much larger range of measurement compared with the conventional systems, and also which preferably can be carried out with enzymes which can be obtained commercially at any time.

Upon further study of the specification and appended claims, further objects and advantages of this invention will become apparent to those skilled in the art.

Surprisingly, it has been found that, under certain conditions, independent reaction of NAD(P)H with a variety of redox indicators is possible. In this context, independent denotes that, for example, the reaction of the second redox indicator (having the lower electrochemical potential) only takes place after the reaction of the first (having the higher electrochemical potential) is substantially complete, so that separate evaluation is possible. This was all the more surprising since it was to be expected that, when the redox indicators are present at one and the same time, interference will occur due to the interaction between the individual substances and due to outside effects (oxygen, test substances, etc.).

Accordingly, these objects have been achieved by this invention by providing a test system having an extended range of measurement for the determination of NAD(P)H, or of substrates or enzymes which react with the formation or consumption of NAD(P)H, comprising, at one and the same time, several substances which act, independently of one another, as electron acceptors with respect to NAD(P)H and which have different electrochemical potentials.

The present invention also relates to procedures for the determination of NAD(P)H, or of substrates or enzymes which react with the formation or consumption of NAD(P)H, in aqueous solution, comprising treating a sample solution at one and the same time with several substances which act, independently of one another, as electron acceptors with respect to NAD(P)H and which have different electrochemical potentials, thereby forming different end products which can be analytically differentiated, and evaluating the latter by a technique of measurement or visually.

DETAILED DISCUSSION

Depending on the type of redox indicator used, the transfer of the electrons can take place directly or using a so-called electron transfer agent. The test system preferably contains electron transfer agents which exert a catalytic effect on the redox indicators. Examples of suitable electron transfer agents include phenazine methosulphate (PMS), phenazine ethosulphate (PES), methoxyphenazine methosulphate (MPMS), Meldola's blue, diaphorase and the like, or mixtures of these substances. Typical effective concentrations include 0.005–0.1 mmol/l.

In principle, suitable redox indicators include all substances which have a higher electrochemical potential than NAD(P)H/NAD(P), and the oxidized and reduced forms of which can unambiguously be differentiated visually, by photometry or using electrochemical procedures. Examples of suitable redox indicators for the test system according to this invention include oxazine and thiazine dyestuffs, tetrazolium salts and the like (See, e.g., U.S. Pat. No. 4,141,688, Proc. Soc. Exp. Biol. 104, 407 (1960) all of whose disclosures are incorporated by reference herein), preferably dichlorophenol-indophenol (DIP), 3-(4-iodophenyl)-2-(4-nitrophenyl)-5-phenyl-2H-tetrazolium chloride (INT) or 3-(4,5-dimethylthioazol-2-yl)-2,5-diphenyl-2H-tetrazolium bromide (MTT). The use of these redox indicators in dehydrogenase test systems has hitherto been restricted to systems having only one redox indicator as end product for the analytical measurement (H. U. Bergmeyer, Methoden der enzymatischen Analyse, Verlag Chemie Weinheim/Bergstrasse, 3rd. Ed., 1974, pp 145-153). Surprisingly, it has now been possible to show that test systems having an extended range of measurement can be made available when several redox indicators having different standard potentials are present. Generally, the potentials should differ from one another by at least 0.02. The standard potentials of the redox indicators should preferably be −0.3 to +0.5, in particular −0.3 to +0.3. As a rule, the determination is carried out in buffered aqueous solutions, it being necessary for the pH to be 4.5 to 8.0, preferably 5.0 to 7.0. Examples of buffers suitable for setting up these pH values are phosphate buffers, citrate buffers, 2-N-morpholino-ethanesulphonic acid sodium salt, bis(2-hydroxy-ethyl)aminotris(hydroxymethyl)methane, or piperazine-N,N'-bis(2-ethanesulphonic acid) dipotassium salt and the like, preferably phosphate buffers and citrate buffers.

The selection of the redox indicators used in a particular case for the test system according to this invention is made in accordance with the available capability of differentiating between the measurement signals produced in the given reaction, preferably in accordance with the change in extinction at different wavelengths (photometric evaluation) or with the change in color of the test solution (visual evaluation). In the latter case, combinations of redox indicators, one form of each of which is colorless or only weakly colored, are especially suitable. Some preferred redox indicators and their normal potentials at a pH of 7 and the corresponding color changes are listed below. Effective concentrations of redox indicators will vary with the indicator and the sample system but typically will be in the range of 0.01–0.5 mmol/1.

| Substance | Potential at pH 7.0 | Color of the oxidized form | Color of the reduced form |
|---|---|---|---|
| NADH | −0.32 | | |
| DIP | +0.23 | blue | colorless |
| MTT | +0.11 | colorless | blue |
| INT | +0.09 | colorless | red |
| Thionine | +0.06 | violet | colorless |
| Methylene blue | +0.01 | blue | colorless |

It is clear from the table that the combination of redox indicators DIP/INT has a color transition from blue to colorless in the first stage and from colorless to red in the second stage and is thus particularly advantageous. The two substances show marked differences in their absorption spectra and in the visual color impressions both between the oxidized and reduced forms of each substance and between the substances themselves. Reaction of the two substances mixed with NAD(P)H leads to independent reaction of DIP and INT and thus to a range of measurement which is considerably extended compared with each system containing only one of these substances. The substance having the higher normal potential (DIP) reacts almost completely before the second substance (INT) reacts. In a determination of NAD(P)H using DIP as the only redox indicator, the concentration range covered is up to about 0.26 mmol/1, with INT the range is up to about 0.13 mmol/1, and with a combination of DIP and INT, the range is up to about 0.55 mmol/1. Using the test system according to this invention, the range of concentration of NAD(P)H covered is increased by from double to more than 4 times. The photometric evaluation can be carried out, for example, by recording the extinction at two different wavelengths (460 and 650 nm). On a visual evaluation, a further increase in the color stages obtained can be produced by adding a so-called background dyestuff (for example titanium yellow) in an effective concentration, e.g., 0.01–0.5 mmol/1. The upper limit of the concentration of NAD(P)H which can be measured using one redox indicator only is based on the characteristics of the instrument used.

On combination of the redox indicators INT and thionine, due to the relative standard potentials, first INT and then thionine is reduced. Depending on the evaluation procedure selected, a wide variety of combinations of redox indicators can be used in the procedure according to this invention.

The test system according to this invention can, in principle, be used for all determinations of NAD(P)H and for all reactions consuming or forming NAD(P)H. The samples to be investigated are preferably body fluids, such as serum, plasma, urine etc. The procedure according to this invention is otherwise carried out in the manner customary for enzymatic methods, in general the reaction converting NAD(P)H being initially allowed to go to completion and then the formed or consumed NAD(P)H being determined. Obviously, in the case of reactions forming NAD(P)H, direct coupling is also possible. Moreover, enzyme activities can be determined by stopping the reaction at a specific time and determining the NAD(P)H formed or consumed in this time. The redox indicators are preferably added to the sample solution at the same time; addition at different times is also possible.

When the test system of this invention is used to measure production or consumption of NAD(P)H in a substrate- or enzyme-based determination, it will usually be preferred to wait a readily determined minimum length of time to avoid unpreferred interference.

Calibration of the test system of this invention can be accomplished fully conventionally, e.g., by preparation of standard curves for the given reaction conditions, e.g., as effected in the following examples.

The test system according to this invention is also suitable, in the form of absorbent materials impregnated with it, as an indicator for the determination of NAD(P)H. Suitable materials include all those inert absorbent carriers customarily in use for such tests. Most widespread is the utilization of filter paper, but other absorbent cellulose or synthetic resin products can likewise be employed. The Test system is usually present in a saturated state.

As can be seen, "test system" herein has the broadest interpretation and includes unitary packaging of the individual components in separate vials or other containers (e.g., in kit form) or in combined form, e.g., in a single aqueous solution and/or absorbed in an absorbent, or in any other appropriate form.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Determination of NAD(P)H

The following three mixtures are prepared:

| Mixture A | Mixture B | Mixture C |
|---|---|---|
| 0.01 mmol/l PMS | 0.01 mmol/l PMS | 0.01 mmol/l PMS |
| 0.25 mmol/l DIP | 0.2 mmol/l INT | 0.2 mmol/l INT |
| 0.025 mmol/l titanium yellow | 0.025 mmol/l titanium yellow | 0.25 mmol/l DIP |
|  |  | 0.025 mmol/l titanium yellow |
| 0.15 mol/l citrate buffer pH 5.8 | 0.15 mol/l citrate buffer pH 5.8 | 0.15 mol/l citrate buffer pH 5.8 |

Various amounts of NADH (NADPH) are added to 2 ml of each of these mixtures. After 10 minutes in each instance, the extinctions at 460 and 650 nm and the color impression of each test solution are determined. The following results are obtained for the color impression depending on the concentration of NADH or NADPH used in the total test solution:

| NADH (NADPH) (mmol/l) | Resulting color impression of the test solution | | |
|---|---|---|---|
|  | Mixture A | Mixture B | Mixture C |
| 0 | deep blue | yellow | deep blue |
| 0.05 | dark blue | orange | dark blue |
| 0.09 | blue | brown | blue |
| 0.13 | light blue | red | light blue |
| 0.17 | blue-green |  | blue-green |
| 0.22 | green |  | green |
| 0.24 | yellow-green |  | yellow-green |
| 0.26 | yellow |  | ochre |
| 0.27 |  |  | orange |
| 0.30 |  |  | brown |
| 0.34 |  |  | red-brown |
| 0.38 |  |  | red |
| 0.55 |  |  | dark red |

The changes in the extinctions in each test solution are shown in FIG. 1.

While a visual determination of the concentration of NADH in the range up to a maximum of 0.25 mmol/l is possible with mixtures A and B, a determination up to 0.55 mmol/l is possible with mixture C.

EXAMPLE 2

Determination of NADH

Various amounts of NADH are added to 2 ml of a solution containing:
- 0.01 mmol/l of MPMS
- 0.2 mmol/l of INT
- 0.03 mmol/l of thionine and
- 0.15 mol/l of a citrate buffer, pH 5.2.

After 10 minutes, the extinctions of each test solution at 460 and 600 nm are measured. The results obtained, as a function of the concentration of NADH used in the total test solution, are shown in FIG. 2.

The range of measurement for the determination of NADH obtained for the test mixture containing two dyestuffs is about double that of corresponding test mixtures containing only one dyestuff.

EXAMPLE 3

Determination of NADH

The following mixtures are prepared:

| Mixture A | Mixture B |
|---|---|
| 0.01 mmol/l Meldola's blue | 0.01 mmol/l Meldola's blue |
| 0.25 mmol/l DIP | 0.25 mmol/l DIP |
| 0.025 mmol/l titanium yellow | 0.2 mmol/l INT |
| 0.15 mol/l citrate buffer pH 5.8 | 0.025 mmol/l titanium yellow |
|  | 0.15 mol/l citrate buffer pH 5.8 |

Various amounts of NADH are added to 2 ml of each of the mixtures. The color impression of each test solution is determined after 10 minutes in each instance. The following results are obtained for the color impression, depending on the concentration of NADH used in the total test solution:

| NADH (mmol/l) | Resulting color impression of the test solution | |
|---|---|---|
|  | Mixture A | Mixture B |
| 0 | deep blue | deep blue |
| 0.10 | turquoise | turquoise |
| 0.20 | dark green | dark green |
| 0.25 | pale green | pale green |
| 0.30 |  | pale brown |
| 0.35 |  | pale red-violet |
| 0.40 |  | wine red |
| 0.50 |  | dark red |

While visual determination of the concentration of NADH is possible in the range up to 0.25 mmol/l with mixture A, determination up to 0.5 mmol/l is possible with mixture B.

EXAMPLE 4

Determination of urea in serum

25 μl serum samples, each having different contents of urea (adjusted by addition of urea, and checked with a standard method) are each added to 1.5 ml of reaction solution containing:
- 0.03 mol/l of phosphate buffer, pH 7.6
- 2.2 mmol/l of ADP
- 4.0 mmol/l of ketoglutamate
- 0.5 mmol/l of NADH
- 30 KU/l of glutamate dehydrogenase and
- 30 KU/l of urease After 10 minutes, 350 μl of a solution containing:
- 0.35 mol/l of citrate buffer, pH 5.8
- 0.05 mmol/l of PMS
- 1.34 mmol/l of DIP
- 1.1 mmol/l of INT
- 0.13 mmol/l of titanium yellow and
- 250 U/l of diaphorase is added to each, and after a further 5 to 10 minutes, the color impression of the reaction solution is determined with through-illumination. The results obtained are as follows:

| Urea (mg/dl) | Resulting color impression of the test solution |
|---|---|
| 0 | Red |
| 30 | red-brown |
| 45 | brown |
| 55 | orange |
| 60 | ochre |
| 70 | yellow-green |
| 80 | green |
| 100 | blue-green |
| 120 | pale blue |

| Urea (mg/dl) | Resulting color impression of the test solution |
| --- | --- |
| 150 | dark blue |
| 180 | deep blue |

While visual determinations of urea up to 70 mg/dl can be carried out with a test mixture containing one dyestuff, the system according to this invention permits determinations up to 180 mg/dl.

EXAMPLE 5

Determination of uric acid in urine

200 μl urine samples containing different amounts of uric acid (adjusted by addition of uric acid, and checked by a standard procedure) are added to 1.3 ml of a reaction solution containing:

0.03 mol/l of phosphate buffer, pH 8.5
42 mmol/l of KCl
1.43 mol/l of ethanol
0.5 mmol/l of NADP+
1750 U/l of catalase
150 U/l of aldehyde dehydrogenase and
50 U/l of uricase.

After 20 minutes, 350 μl of a solution, which contains the following constituents:

0.5 mol/l of citrate buffer, pH 5.8
0.05 mmol/l of PES
1.34 mmol/l of DIP
1.10 mmol/l of INT and
0.13 mmol/l of titanium yellow is added to each test solution. After a further 10 minutes, the color impression of the reaction solution is determined with through-illumination. The results obtained are as follows:

| Uric acid (mg/dl) | Resulting color impression of the test solution |
| --- | --- |
| 0 | deep blue |
| 9 | dark blue |
| 15 | blue |
| 21 | light blue |
| 29 | blue-green |
| 37 | green |
| 40 | yellow-green |
| 42 | ochre |
| 45 | brown |
| 50 | red-brown |
| 57 | red |
| 64 | dark red |

While visual determinations of uric acid in a range up to about 40 mg/dl can be carried out with an appropriate test containing only one dyestuff, up to more than 60 mmol/l can still be reliably measured with the system according to the invention.

EXAMPLE 6

Determination of lactate dehydrogenase in serum

100 μl of serum samples containing different activities of LDH (adjusted by addition of LDH, and checked with a standard method) are added to 1.2 ml of a reaction solution containing:

0.03 mol/l of phosphate buffer, pH 7.5
0.6 mmol/l of pyruvate and
0.5 mmol/l of NADH.

After 10 minutes at 25° C., 300 μl of a solution containing:

0.5 mol/l of citrate buffer, pH 5.8
1.34 mmol/l of DIP
1.10 mmol/l of INT
0.05 mmol/l of PMS
0.13 mmol/l of titanium yellow and
4 mmol/l of oxamic acid is added. After a further 10 minutes, the color impression of each total test solution is determined. The results obtained are as follows:

| LDH (U/l) | Resulting color impression of the test solution |
| --- | --- |
| 32 | red |
| 96 | red-brown |
| 160 | brown |
| 210 | orange |
| 225 | ochre |
| 255 | yellow-green |
| 290 | green |
| 370 | blue-green |
| 430 | pale blue |
| 500 | blue |
| 560 | dark blue |
| 640 | deep blue |

While LDH determinations with visual evaluation in a range to a maximum of 225 U/l can be carried out with an appropriate test containing only one dyestuff, determinations up to more than 600 U/l are possible with the test system according to the invention.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A test system useful for providing an extended range of measurement for the determination of NADH, NADPH, NAD+ or NADP+, or of a substrate or enzyme which reacts with the formation or consumption of NADH or NADPH, comprising effective amounts of at least two redox indicators which, independently of each other, act as electron acceptors with respect to NAD(P)H and which each have different electrochemical potentials.

2. A test system of claim 1, wherein the redox indicators have a standard potential of −0.3 to +0.5.

3. A test system of claim 1, wherein the redox indicators have a standard potential of −0.3 to +0.3.

4. A test system of claim 1 further comprising an effective amount of a buffer which maintains a pH of 4.5–8.0.

5. A test system of claim 1 further comprising an effective amount of a buffer which maintains a pH of 5.0–7.0.

6. A test system of claim 5 wherein the buffer is a phosphate buffer, a citrate buffer, 2-N-morpholinoethanesulphonic acid sodium salt, bis(2-hydroxy-ethyl) aminotris(hydroxymethyl)methane, or piperazine-N,N'-bis(2-ethanesulphonic acid) dipotassium salt.

7. A test system of claim 1 further comprising an effective amount of an electron transfer agent.

8. A test system of claim 7 wherein the electron transfer agent is, phenazine methosulphate, phenazine ethosulphate, methoxyphenazine methosulphate, Meldola's blue, diaphorase or a mixture thereof.

9. A test system of claim 1 wherein each redox indicator is dichlorophenol-indophenol or a tetrazolium salt.

10. A test system of claim 1 wherein each redox indicator is dichlorophenol-indophenol, 3-(4-iodo- phenyl)-2-(4-nitrophenyl)-5-phenyl-2H-tetrazolium chloride or 3-(4,5-dimethylthiazol-2-yl)-2,5-diphenyl-2H-tetrazolium bromide.

11. A test system of claim 1 further comprising a background dyestuff.

12. A test system of claim 11 wherein the background dyestuff is titanium yellow.

13. A test system of claim 1 wherein the redox indicators are dichlorophenol-indophenol and 3-(4-iodophenyl)-2-(4-nitrophenyl)-5-phenyl-2H-tetrazolium chloride.

14. A test system of claim 1, wherein said indicators are impregnated within an absorbent material.

15. A method for the determination of NADH, NADPH, NAD+ or NADP+ in an aqueous sample solution, comprising treating the sample solution with at least two system compatible redox substances which act, independently of one another, as electron acceptors with respect to NADH or NADPH and which have different electrochemical potentials, whereby there are sequentially formed corresponding, different end products, and analytically measuring each end product.

16. A method of claim 15 wherein the NADH, NADPH, NAD+ or NADP+ moiety is derived from the presence of a substrate or enzyme which has reacted to form said moiety, and the measurement of said end products constitutes a determination of the substrate or enzyme.

17. A method of claim 15 wherein the measurement is conducted photometrically.

18. A method of claim 15 wherein the measurement is conducted visually.

19. A method of claim 15 wherein the determination is carried out in a buffered aqueous solution of a pH of 4.5–8.0.

20. An absorbent material impregnated with a test system useful for providing an extended range of measurement for the determination of NADH, NADPH, NAD+ or NADP+, or of a substrate or enzyme which reacts with the formation or consumption of NADH or NADPH, comprising effective amounts of at least two redox indicators which, independently of each other, act as electron acceptors with respect to NAD(P)H and which have different electrochemical potentials.

* * * * *